United States Patent
Williams et al.

(10) Patent No.: US 6,180,783 B1
(45) Date of Patent: *Jan. 30, 2001

(54) STABILIZED CARBAPENEM INTERMEDIATES AND IMPROVED PROCESS FOR CARBAPENEM SYNTHESIS

(75) Inventors: John M. Williams, Belle Mead, NJ (US); Renato T. Skerlj, Bellingham, WA (US); Karel M. J. Brands, Hoboken, NJ (US); Ulf H. Dolling, Westfield, NJ (US); Ronald B. Jobson, East Brunswick, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/093,813

(22) Filed: Jun. 9, 1998

Related U.S. Application Data

(60) Provisional application No. 60/049,640, filed on Jun. 16, 1997.

(51) Int. Cl.$^7$ .................................................. C07D 477/20
(52) U.S. Cl. ............................................................. 540/350
(58) Field of Search .............................................. 540/350

(56) References Cited

U.S. PATENT DOCUMENTS

| | | | |
|---|---|---|---|
| 4,269,772 | 5/1981 | Melillo et al. | 540/350 |
| 4,383,946 | 5/1983 | Christensen et al. | 540/350 |
| 4,414,155 | 11/1983 | Liu et al. | 540/350 |
| 4,994,568 | 2/1991 | Christensen | 540/350 |
| 5,478,820 | 12/1995 | Betts et al. | 540/350 |

FOREIGN PATENT DOCUMENTS

97/45430 * 12/1997 (WO) .

OTHER PUBLICATIONS

L. M.Fuentes, et al., *J. Am. Chem. Soc.*, 108, pp. 4675–4676 (1986).
C. Wentrup et al., *J. Am. Chem. Soc.*, 102, pp. 6161–6163 (1980).
D. C. Melillo et al. *Tet Ltr*, 21, p. 2783 (1980).

* cited by examiner

*Primary Examiner*—Mark L. Berch
(74) *Attorney, Agent, or Firm*—Sylvia A. Ayler; Mark R. Daniel

(57) ABSTRACT

A stabilized carbapenem intermediate compound represented by the formula 1:

or a salt thereof is disclosed, wherein P represents a carboxyl protecting group and X represents a charge balancing group.

In addition, a process for synthesizing a compound represented by formula 2:

is disclosed wherein $X^+$ is a charge balancing group, comprising: deprotecting a compound of the formula 1 to produce a compound 2.

8 Claims, No Drawings

STABILIZED CARBAPENEM INTERMEDIATES AND IMPROVED PROCESS FOR CARBAPENEM SYNTHESIS

This application claims the benefit of U.S. Provisional Application No. 60/049,640, filed Jun. 16, 1997.

BACKGROUND OF THE INVENTION

The present invention relates to stabilized forms of carbapenem compounds and intermediates used in their preparation. Such stabilized forms are particularly useful in reducing the degradation associated with the preparation of carbapenems and improving overall yields.

SUMMARY OF THE INVENTION

A stabilized carbapenem intermediate compound represented by the formula 1:

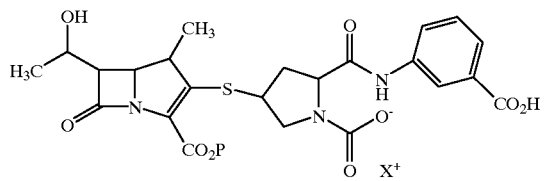

1 or a salt thereof is disclosed wherein P represents a carboxyl protecting group and X represents a charge balancing group.

In addition, a process for synthesizing a compound represented by formula 2:

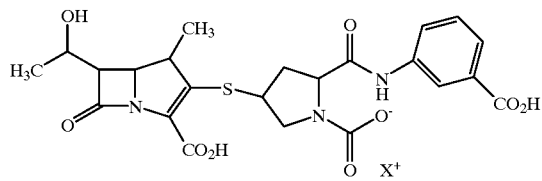

2 or a pharmaceutically acceptable salt or ester thereof, is disclosed wherein X is a charge balancing group, comprising:

deprotecting a compound of the formula 1 to produce a compound of formula 2.

DETAILED DESCRIPTION OF THE INVENTION

As used herein, the term "stabilized form" refers to compounds which have a carbamate group formed at the pyrrolidine nitrogen atom, as shown in compound 1. The carbamate 1 can be obtained as shown below in Flow Sheet A.

FLOW SHEET A-1

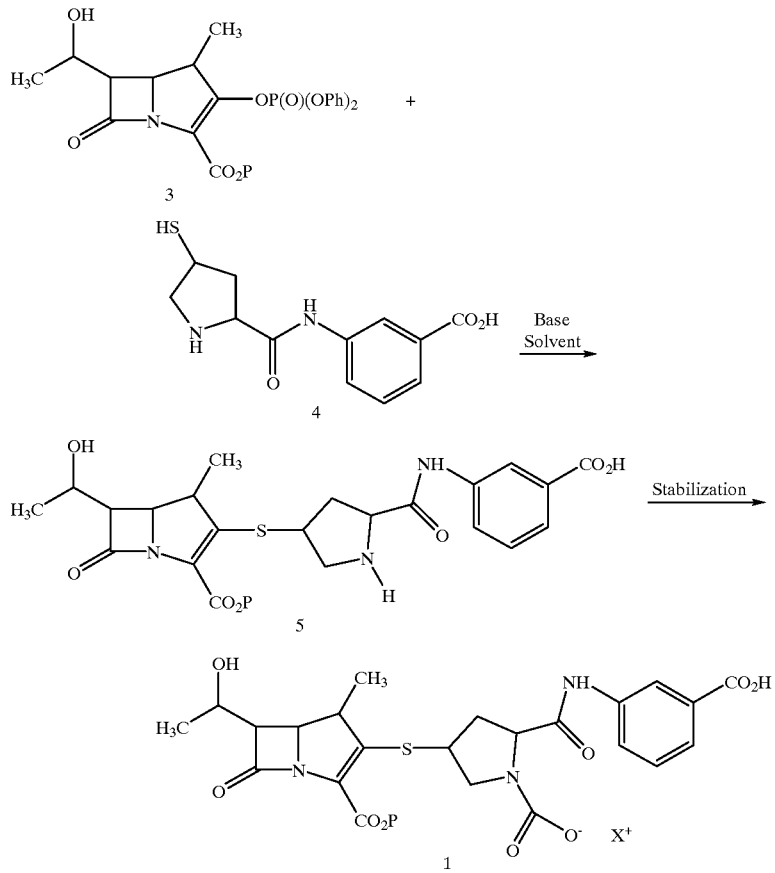

Flow sheet A-2 below provides a preferred process as it relates to 1β-methyl carbapenems.

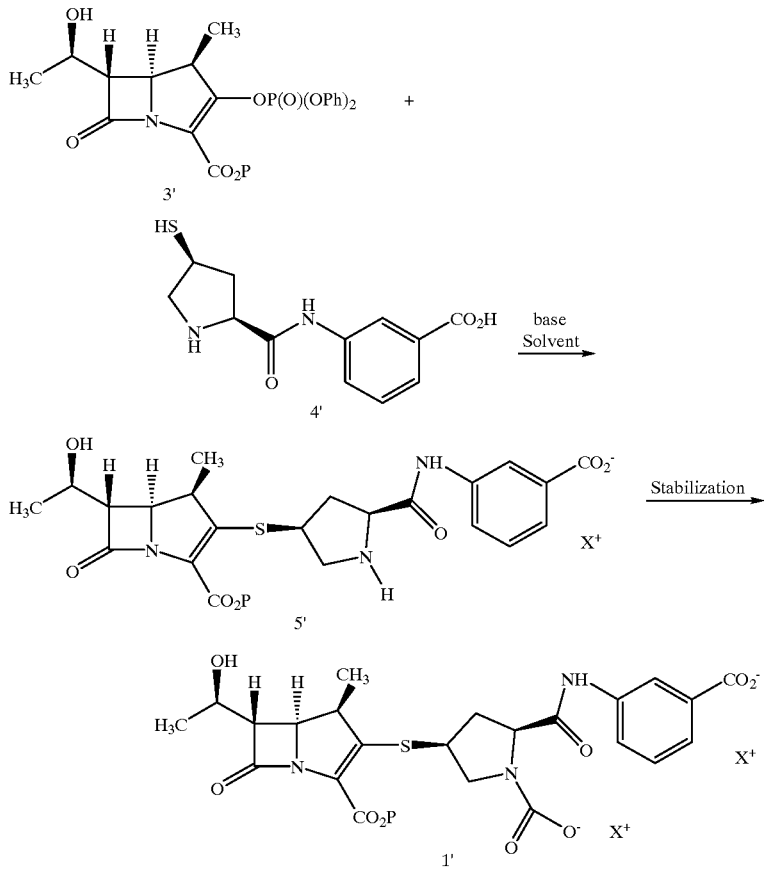

FLOW SHEET A-2

Compounds 3 and 3' can be obtained using the disclosures contained in U.S. Pat. Nos. 4,994,568 granted on Feb. 19, 1991; 5,478,820 granted on Dec. 26, 1995; 4,269,772 granted on May 26, 1981; 4,350,631 granted on Sep. 21, 1982; 4,383,946 granted on May 17, 1983; 4,414,155 granted on Nov. 8, 1983; Tet. Let. 21, 2783 (1980); J. Am. Chem. Soc. 108, 6161 (1980); and J. Am. Chem. Soc. 108, 4675 (1986). The teachings of these references are incorporated by reference.

Compounds 4 and 4' can be obtained using the disclosure contained in Betts, et al. U.S. Pat. No. 5,478,820.

The compound of formula 1 or a salt thereof is produced by reacting the enol phosphate 3 and side chain precursor 4 in the presence of a base. This reaction is typically conducted at reduced temperature, e.g., about −30° C. to about −50° C. Bases which are suitable for the above reaction include organic as well as inorganic bases. A preferred base for use herein is sodium hydroxide.

The reaction can be conducted in an organic solvent, e.g., N-ethyl pyrrolidinone, N-methyl pyrrolidinone, N,N-dimethylformamide and the like.

Any excess base which is present in the reaction can be quenched, such as by the addition of an ester, e.g., isopropyl acetate or ethyl acetate.

After coupling, the carbapenem is stabilized by combining the carbapenem with a carbon dioxide source. This provides a transient structure of formula 1 where $X^+$ represents a charge balancing counterion. Examples of carbon dioxide sources include carbon dioxide gas, bicarbonates, such as sodium and potassium bicarbonate, and carbonates such as sodium and potassium carbonate.

Stabilization can be conducted under substantially neutral to slightly basic conditions, e.g., about pH 7.0 to about 8.5.

After stabilization, the carbapenem is subject to deprotection, thus removing the 3-carboxyl protecting group. The pyrrolidine nitrogen is maintained in the carbamate form during hydrogenolysis.

A preferred deprotection reaction is hydrogenolysis, which can be conducted using hydrogen gas or a compound which forms hydrogen.

Hydrogenolysis effectively removes the protecting group from the 3-carboxylate without substantially disrupting the β-lactam ring or the stabilized carbamate form of the pyrrolidine amine.

Hydrogenolysis is typically conducted in the presence of a metal catalyst. The preferred reaction involves $H_2$ gas with a palladium (Pd/C) catalyst. If necessary, base can be added. A preferred base is sodium hydroxide or sodium bicarbonate.

The stability of the pyrrolidine N-carbamate is pH dependent and is readily converted to the unsubstituted pyrrolidine amine or ammonium salt under neutral to mildly acidic conditions. The carbapenem, or a salt or ester thereof, is then suitable for isolation, formulation or elaboration.

Carbon dioxide sources, as used herein, refer to carbon dioxide gas as well as compounds which produce carbon dioxide upon dissolution. Representative examples include carbonates and bicarbonates, such as sodium carbonate, sodium bicarbonate, potassium carbonate and potassium bicarbonate. Preferably the carbonates and bicarbonates are used. Most preferably, the carbon dioxide source is sodium bicarbonate.

The carbon dioxide source can alternatively be included in the reaction medium prior to or during the deprotection reaction. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenolysis.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable protecting groups are known in the art. See, e.g., T. W. Greene, *Protective Groups in Organic Synthesis*, John Wiley & Sons, Inc., 1981 (Chapters 2 and 5).

Numerous salt-forming ions are recited in Berge, S. M., et al. *J. Pharm. Sci*. 66(1): 1–16 (1977), the teachings of which are incorporated herein by reference. The charge balancing group X, maintains overall charge neutrality. Preferably X represents a pharmaceutically acceptable salt forming cation.

Preferred salt-forming cations are selected from the group consisting of: sodium, potassium, calcium and magnesium.

More preferably the salt forming cation is a member selected from the group consisting of: $Na^+$, $Ca^{+2}$ and $K^+$.

The salt forming cations mentioned above provide electronic balance and overall charge neutrality. From zero to three positively charged counterions may be present, depending upon the number of charged moieties on the carbapenem. This is largely a function of pH, since at low pH, protonation of the negatively charged moieties may occur. Different counterions may also be included in the overall composition. Hence, for example, calcium and sodium could be included together in the pharmaceutical composition to provide overall charge neutrality. The counterions can thus be varied within wide limits. Generally the counterion or counterions are pharmaceutically acceptable cationic species.

The compounds formed in the present invention have asymmetric centers and occur as racemates, racemic mixtures, and as individual diastereomers. The processes of synthesizing all such isomers, including optical isomers, are included in the present invention.

EXAMPLE 1

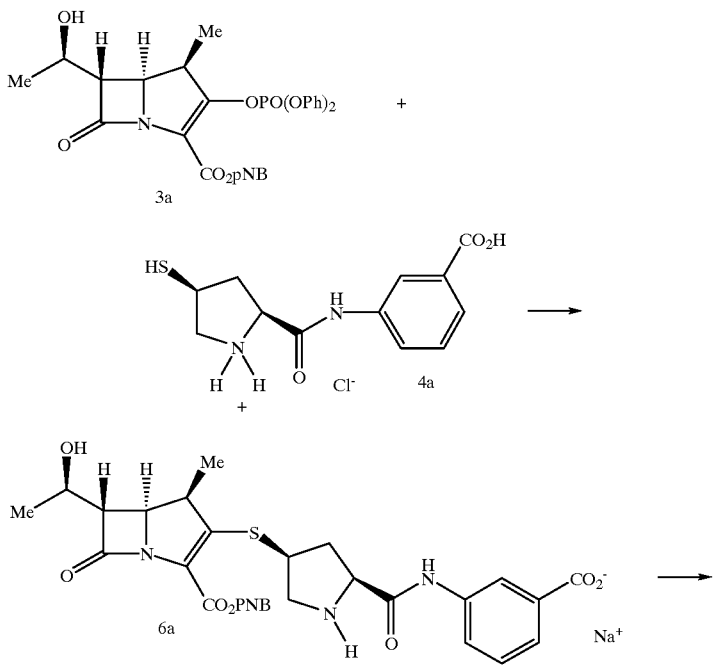

-continued

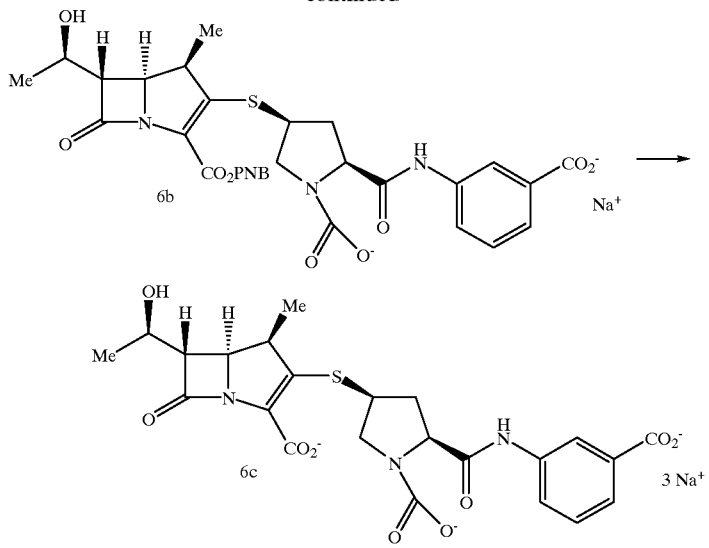

Enol phosphate 3a (150 g) was dissolved in 575 mL of N-ethyl-pyrrolidinone and the resulting solution was cooled to −40 to −45° C. The hydrochloride salt 4a (1.01 equiv) was separately dissolved in a mixture of N-ethylpyrrolidinone (330 mnL) and water (40 mL) at about 20° C. with vacuum degassing. A solution of 8 N sodium hydroxide (3.0 equiv) was added to the solution of the side chain maintaining the temperature below 30° C. This solution was added to the solution of the enol phosphate 3a at −35 to −45° C. After 2 h at −40° C. the mixture containing 6a was diluted with 600 mL of dichloromethane and transferred to a mixture of 1.0 L of water containing 55 g of sodium bicarbonate, 32.5 g of 5% palladium on carbon catalyst and 600 mL of dichloromethane producing 6b. The pH was adjusted to 7-8 using carbon dioxide.

The mixture was stirred under 50 psi of hydrogen gas for 2 h at 5–10° C. controlling the pH at about 7.2 with 1 N sodium hydroxide. After 3 h the pH of the mixture was adjusted to 5.5 using 10% HCl (500 mL) and the mixture was filtered through solka floc washing with water. The layers were separated and the pH of the aqueous layer was adjusted from 5.5 to 6.4 using 1 N sodium bicarbonate (320 mL). Following extraction with dichloromethane, the aqueous solution containing product in the stabilized form was purified using a hydrophobic resin eluting with 0.05 M sodium bicarbonate at about 5° C. producing 6c.

The solution was concentrated at about 5° C. by nanofiltration using a Millipore Nanomax-50 Helicon RO60 membrane to give a solution of the product 6c in the stabilized form at about 120 g/L.

EXAMPLE 2

Using the material from Example One, the pH was adjusted from 7.5 to 5.50 using glacial acetic acid and the product was crystallized by adding methanol and 1-propanol, affording 70 g of the monosodium salt after filtration.

While certain preferred embodiments of the invention have been described herein in detail, numerous alternative embodiments are contemplated as falling within the scope of the appended claims. Consequently the invention is not to be limited thereby.

What is claimed is:

1. A stabilized carbapenem intermediate compound represented by the formula 1:

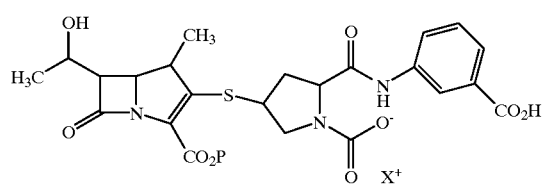

or a salt thereof, wherein P represents a carboxyl protecting group and X represents a charge balancing group.

2. A stabilized carbapenem intermediate compound in accordance with claim 1 wherein P is selected from the group consisting of: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl) ethyl, phenacyl, p-methoxybenzyl, acetonyl, p-methoxyphenyl, 4-pyridylmethyl and t-butyl.

3. A stabilized carbapenem intermediate compound in accordance with claim 2 wherein P is selected from allyl and p-nitrobenzyl.

4. A stabilized carbapenem intermediate compound in accordance with claim 1 wherein X⁺ represents a member selected from the group consisting of: sodium and potassium.

5. A process for synthesizing a compound represented by formula 2:

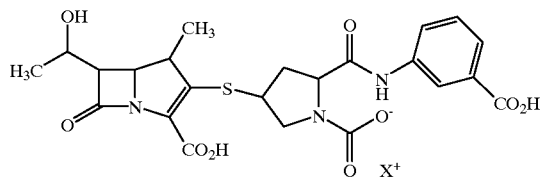

or a pharmaceutically acceptable salt thereof, wherein X is a charge balancing group, comprising:

deprotecting a compound of formula 1:

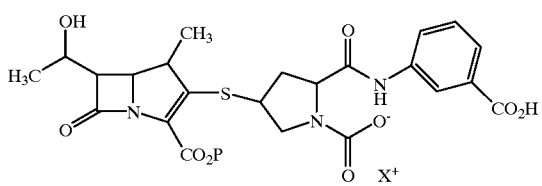

to produce a compound of formula 2.

6. A process in accordance with claim 5 wherein the deprotection is conducted using hydrogen gas.

7. A process in accordance with claim 6 further comprising purifying the compound, said purification is conducted using hydrophobic resin chromatography.

8. A process in accordance with claim 6 further comprising concentrating the compound in solution using a nanofiltration membrane.

* * * * *